(12) United States Patent
Yang

(10) Patent No.: US 6,844,357 B2
(45) Date of Patent: Jan. 18, 2005

(54) SUBSTITUTED QUINOLIN-2-ONE DERIVATIVES USEFUL AS ANTIPROLIFERATIVE AGENTS

(75) Inventor: Bingwei V. Yang, Belle Meade, NJ (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/844,646

(22) Filed: Apr. 27, 2001

(65) Prior Publication Data

US 2003/0166675 A1 Sep. 4, 2003

Related U.S. Application Data

(60) Provisional application No. 60/200,834, filed on May 1, 2000.

(51) Int. Cl.⁷ .................. C61K 31/47; C07D 215/16; C07D 215/12
(52) U.S. Cl. .................. 514/312; 514/311; 514/314; 546/154; 546/157; 546/158; 546/173; 546/176
(58) Field of Search ................ 514/312, 311, 514/314; 546/154, 157, 158, 176, 173

(56) References Cited

U.S. PATENT DOCUMENTS

| | | | | |
|---|---|---|---|---|
| 5,968,952 A | * | 10/1999 | Venet et al. | 514/312 |
| 6,037,350 A | * | 3/2000 | Venet et al. | 514/312 |
| 6,169,096 B1 | * | 1/2001 | Venet et al. | 514/312 |
| 6,365,600 B1 | * | 4/2002 | End et al. | 514/312 |
| 6,620,387 B1 | * | 9/2003 | Sy | 422/194 |

FOREIGN PATENT DOCUMENTS

| | | | |
|---|---|---|---|
| WO | WO 97/16443 | * | 5/1997 |
| WO | WO 97/21701 | * | 6/1997 |
| WO | WO 98/55124 | * | 12/1998 |

* cited by examiner

*Primary Examiner*—D. Margaret Seaman
(74) *Attorney, Agent, or Firm*—Peter C. Richardson; Krishna G. Banerjee; Garth Butterfield

(57) ABSTRACT

The present invention relates to compounds of formulas 1 and 2

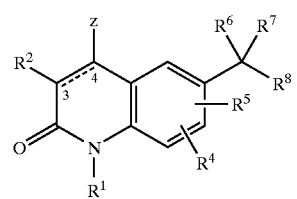

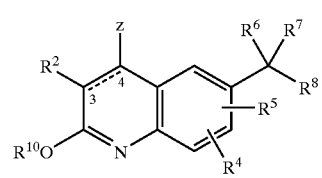

wherein $R^1$, $R^2$, $R^4$, $R^5$, $R^6$, $R^7$, $R^8$, $R^{10}$ and Z are as defined herein. The present invention also relates to pharmaceutical compositions containing the above compounds and to methods of treating hyperproliferative disorders, such as cancer, in a mammal by administering the above compounds.

11 Claims, No Drawings

SUBSTITUTED QUINOLIN-2-ONE DERIVATIVES USEFUL AS ANTIPROLIFERATIVE AGENTS

This application claims priority from U.S. Provisional Patent Application No. 60/200,834, filed May 1, 2000.

BACKGROUND OF THE INVENTION

This invention relates to a series of heteroaryl-substituted quinolin-2-one derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as agents to combat tumors in which Ras contributes to transformation. Mutated, oncogenic forms of Ras are frequently found in many human cancers, most notably in more than 50% of colon and pancreatic carcinomas (Kohl et al., *Science*, Vol. 260, 1834 to 1837, 1993). The compounds of the present invention exhibit activity as inhibitors of the enzyme farnesyl protein transferase and are therefore believed to be useful as anti-cancer and anti-tumor agents. Further, the compounds of the present invention may be active against any tumors that proliferate by virtue of farnesyl protein transferase.

Other compounds that are indicated as having activity inhibiting farnesyl protein transferase are referred to in International Publication Number WO 97/21701, entitled "Farnesyl Protein Transferase Inhibiting (Imidazol-5-yl) methyl-2-quinolinone Derivatives", which has an International Publication Date of Jun. 19, 1997; in International Publication Number WO 97/16443, entitled "Farnesyl Transferase Inhibiting 2-Quinolone Derivatives", which has an International Publication Date of May 9, 1997; PCT International application number PCT/IB99/01393, filed Aug. 5, 1999, entitled "2-Quinolone derivatives Useful as Anticancer Agents"; PCT international application number PCT/IB99/01398, filed Aug. 6, 1999, entitled "Alkynyl-Substituted Quinolin-2-one Derivatives Useful as Anticancer Agents"; PCT international application number PCT/IB00/00121, filed Feb. 4, 2000 (Attorney docket number PC 10198A); U.S. provisional patent application No. 60/170,119, filed Dec. 10, 1999 (Attorney docket number PC 10443); and U.S. provisional patent application No. 60/177,718, filed Jan. 21, 2000 (Attorney docket number PC 10794), all of which are incorporated herein by reference in their entireties.

SUMMARY OF THE INVENTION

The present invention relates to compounds of formulas 1 and 2

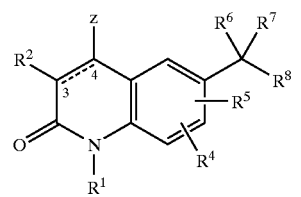

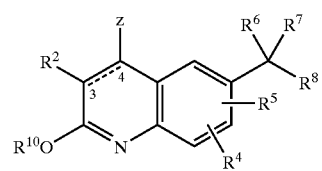

and to pharmaceutically acceptable salts, solvates and prodrugs thereof wherein:

the dashed lines in formulas 1 and 2 indicate an optional second bond connecting C-3 and C-4 of the quinolin-2-one rings;

Z is an aromatic 4 to 10 membered heterocyclic group, substituted with 1 to 4 $R^3$ substituents;

$R^1$ is selected from H, $C_1$–$C_{10}$ alkyl, —$(CR^{11}R^{12})_qC(O)$ $R^{10}$, —$(CR^{11}R^{12})_qC(O)OR^9$, —$(CR^{11}R^{12})_qOR^{10}$, —$(CR^{11}R^{12})_qC(R^{11})(R^{12})SO_2R^9$, —$(CR^{11}R^{12})_t$ $(C_3$–$C_{10}$ cycloalkyl), —$(CR^{11}R^{12})_t(C_6$–$C_{10}$ aryl), and —$(CR^{11}R^{12})_t$(4 to 10 membered heterocyclic), wherein each t is independently an integer from 0 to 5 and each q is independently an integer from 1 to 5; said cycloalkyl, aryl and heterocyclic $R^1$ groups are optionally fused to a $C_6$–$C_{10}$ aryl group, a $C_5$–$C_8$ saturated cyclic group, or a 4 to 10 membered heterocyclic group; and the foregoing $R^1$ groups, except H but including any optional fused rings referred to above, are optionally substituted with 1 to 4 $R^3$ groups;

R is halo, cyano, —$C(O)OR^{10}$, or a group selected from the substituents provided in the definition of $R^{10}$;

each $R^3$, $R^4$ and $R^5$ is independently selected from H, $R^{10}$, $C_2$–$C_{10}$ alkenyl, $C_2$–$C_{10}$ alkynyl, halo, cyano, nitro, trifluoromethyl, trifluoromethoxy, azido, —$OR^{10}$, —$C(O)R^{10}$, —$C(O)OR^{10}$, —$NR^{11}C(O)OR^{10}$, —$OC(O)R^{10}$, —$NR^{11}SO_2R^{10}$, —$SO_2NR^{10}R^{11}$, —$NR^{11}C(O)R^{10}$, —$C(O)NR^{10}R^{11}$, —$NR^{10}R^{11}$, —$CH$=$NOR^{10}$, —$S(O)_jR^{10}$, —$(CR^{11}R^{12})_tC$≡$CR^{10}$, and —$(CR^{11}R^{12})_t$ $C$≡$CR^{13}$, wherein each t is independently an integer from 0 to 5 and each j is independently an integer from 0 to 2; said alkyl, alkenyl, alkynyl, cycloalkyl, aryl, and heterocyclic moieties of the foregoing $R^3$, $R^4$, and $R^5$ groups are optionally substituted by 1 to 3 substituents independently selected from halo, cyano, nitro, trifluoromethyl, trifluoromethoxy, azido, —$NR^{11}SO_2$ $(C_1$–$C_6$ alkyl), —$SO_2NR^{11}R^{12}$, —$C(O)R^{10}$, —$C(O)$ $OR^{10}$, —$OC(O)R^{10}$, —$NR^{11}C(O)OR^{10}$, —$NR^{11}C(O)$ $R^{10}$, —$C(O)NR^{11}R^{12}$, —$NR^{11}R^{12}$, hydroxy, $C_1$–$C_6$ alkoxy, $C_1$–$C_{10}$ alkyl, $C_2$–$C_{10}$ alkenyl, $C_2$–$C_{10}$ alkynyl, —$(CR^{11}R^{12})_t(C_6$–$C_{10}$ aryl), —$(CR^{11}R^{12})_t(C_3$–$C_{10}$ cycloalkyl), and —$(CR^{11}R^{12})_t$(4 to 10 membered heterocyclic), wherein each t is independently an integer from 0 to 5;

$R^6$ is H, cyano, —$(CR^{11}R^{12})_t$(4 to 10 membered heterocyclic) wherein t is an integer from 0 to 5, —OR$^{10}$, —OC(O)R$^{10}$, —NR$^{10}$R$^{11}$, —NR$^{11}$C(O)H, —C(O)OR$^{10}$, or —SR$^{10}$, wherein heterocyclic groups of said R$^6$ groups are optionally substituted by 1 to 4 R$^3$ groups;

R$^7$ is —(CR$^{11}$R$^{12}$)$_t$(imidazolyl) or —(CR$^{11}$R$^{12}$)$_t$ (pyridinyl), wherein each t is an integer from 0 to 5 and said imidazolyl and pyridinyl moieties are optionally substituted by up to 2 R$^3$ substituents;

R$^8$ is phenyl or an aromatic 4 to 10 membered heterocyclic group, and said R$^8$ group is optionally substituted by 1 to 4 R$^3$ substituents;

each R$^{10}$ is independently selected from H, C$_1$–C$_{10}$ alkyl, —(CR$^{11}$R$^{12}$)$_t$(C$_3$–C$_{10}$ cycloalkyl), —(CR$^{11}$R$^{12}$)$_t$ (C$_6$–C$_{10}$ aryl), and —(CR$^{11}$R$^{12}$)$_t$(4 to 10 membered heterocyclic); wherein each t is independently an integer from 0 to 5 and said cycloalkyl, aryl and heterocyclic R$^{10}$ groups are optionally fused to a C$_6$–C$_{10}$ aryl group, a C$_5$–C$_8$ saturated cyclic group, or a 4 to 10 membered heterocyclic group; and the foregoing R$^{10}$ substituents, except H but including any optional fused rings, are optionally substituted by 1 to 3 substituents independently selected from halo, cyano, nitro, trifluoromethyl, trifluoromethoxy, azido, —C(O)R$^{11}$, —C(O)OR$^{11}$, —OC(O)R$^{11}$, —NR$^{11}$C(O)R$^{12}$, —C(O) NR$^{11}$R$^{12}$, —NR$^{11}$R$^{12}$, hydroxy, C$_1$–C$_6$ alkyl, and C$_1$–C$_6$ alkoxy;

each R$^{11}$ and R$^{12}$ is independently H or C$_1$–C$_6$ alkyl, and where R$^{11}$ and R$^{12}$ are as —(CR$^{11}$R$^{12}$)$_q$ or —(CR$^{11}$R$^{12}$)$_t$ each is independently defined for each iteration of q or t in excess of 1;

R$^{13}$ is selected from the list of substituents provided in the definition of R$^{10}$ and —SiR$^{14}$R$^{15}$R$^{16}$; and, R$^{14}$, R$^{15}$ and R$^{16}$ are each independently selected from the substituents provided in the definition of R$^{10}$ except at least one of R$^{14}$, R$^{15}$ and R$^{16}$ is not H.

Preferred compounds of formula 1 include those wherein wherein Z is a pyridine or a thiophene group, including pyridine or thiophene groups substituted with from 1 to 4 R$^3$ substituents; R$^1$ is H, C$_1$–C$_6$ alkyl, or cyclopropylmethyl; R$^2$ is H; and R$^6$ is —NR$^{10}$R$^{11}$, —OR$^{10}$, or a heterocyclic group selected from triazolyl, imidazolyl, pyrazolyl, and piperidinyl, wherein said heterocyclic group is optionally substituted by an R$^3$ group. More preferred compounds include those wherein R$^7$ is imidazolyl optionally substituted by C$_1$–C$_6$ alkyl; R$^6$ is hydroxy, amino, or triazolyl; R$^8$ is phenyl substituted by 1 to 2 R$^3$ groups; and R$^4$, and R$^5$ are each independently selected from H and halo.

Other preferred compounds of formula 1 include those wherein R$^1$ is —(CR$^{11}$R$^{12}$)$_t$(C$_3$–C$_{10}$ cycloalkyl) wherein t is an integer from 0 to 3; R$^2$ is H; and R$^6$ is —NR$^{10}$R$^{11}$, —OR$^{10}$, or a heterocyclic group selected from triazolyl, imidazolyl, pyrazolyl, and piperidinyl, wherein said heterocyclic group is optionally substituted by an R$^3$ group. More preferred compounds include those wherein R$^7$ is imidazolyl optionally substituted by C$_1$–C$_6$ alkyl; R$^6$ is hydroxy, amino, or triazolyl.

Preferred compounds of formula 2 include those wherein Z is a pyridine or a thiophene group, including pyridine or thiophene groups substituted with from 1 to 4 R$^3$ substituents; R$^2$ is H; R$^6$ is —NR$^{10}$R$^{11}$, —OR$^{10}$ or triazolyl. More preferred compounds include those wherein R$^7$ is imidazolyl optionally substituted by C$_1$–C$_6$ alkyl; R$^6$ is hydroxy or amino; R$^8$ is phenyl substituted by 1 to 2 R$^3$ groups; and R$^4$ and R$^5$ are each independently selected from H and halo.

Preferred compounds of the present invention include the following:
(4-Chloro-phenyl)-[2-methoxy-4-(5-methyl-thiophen-2-yl)-quinolin-6-yl]-(3-methyl-3H-imidazol-4-yl)-methanol;
6-[(4-Chloro-phenyl)-hydroxy-(3-methyl-3H-imidazol-4-yl)-methyl]-1-methyl-4-(5-methyl-thiophen-2-yl)-1H-quinolin-2-one;
6-[Amino-(4-chloro-phenyl)-(3-methyl-3H-imidazol-4-yl)-methyl]-1-methyl-4-(5-methyl-thiophen-2-yl)-1H-quinolin-2-one;
6-[(4-Chloro-phenyl)-hydroxy-(3-methyl-3H-imidazol-4-yl)-methyl]-4-(5-chloro-thiophen-2-yl)-1-methyl-1H-quinolin-2-one;
and the pharmaceutically acceptable salts, solvates and prodrugs of the foregoing compounds.

The present invention also relates to a method of preparing a compound of formula 1 as described above, wherein R$^1$ of formula 1 is H, which comprises hydrolysing a compound of formula 2'

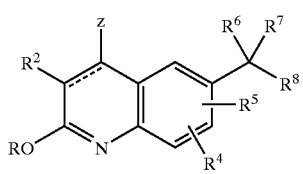

wherein R is C$_1$–C$_6$ alkyl and Z, R$^2$, R$^4$, R$^5$, R$^6$, R$^7$ and R$^8$ are as defined for formula 1 above.

This invention also relates to a method of treating abnormal cell growth in a mammal, including a human, comprising administering to said mammal an amount of a compound of the formula 1 or 2, as defined above, or a pharmaceutically acceptable salt, solvate or prodrug thereof, that is effective in treating said abnormal cell growth.

The invention also relates to a method for the treatment of abnormal cell growth in a mammal which comprises administering to said mammal a therapeutically effective amount of a compound of formulas 1 or 2, as defined above, or a pharmaceutically acceptable salt, solvate or prodrug thereof, in combination with another chemotherapeutic agent. In one embodiment, the chemotherapeutic agent is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention further relates to a method for treating abnormal cell growth in a mammal which method comprises administering to the mammal an amount of a compound of formula 1 or 2, or a pharmaceutically acceptable salt, solvate or prodrug thereof, in combination with radiation therapy, wherein the amount of the compound of formula 1 or 2, in combination with the radiation therapy, is effective in treating abnormal cell growth in the mammal. Techniques for administering radiation therapy are known in the art, and these techniques can be used in the combination therapy described herein.

It is believed that the compounds of formula 1 and 2 may render cells associated with abnormal cell growth more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula 1 or 2, or a pharmaceutically acceptable salt, solvate or prodrug thereof, that is effective in sensitizing said cells to treatment with radiation.

This invention also relates to a pharmaceutical composition for treating abnormal cell growth in a mammal, including a human, comprising an amount of a compound of the formula 1 or 2, or a pharmaceutically acceptable salt, solvate or prodrug thereof, that is effective in treating said abnormal cell growth, and a pharmaceutically acceptable carrier.

The invention also relates to a pharmaceutical composition for treating abnormal cell growth in a mammal which comprises a therapeutically effective amount of a compound of formula 1 or 2, or a pharmaceutically acceptable salt, solvate or prodrug thereof, in combination with another chemotherapeutic agent, and a pharmaceutically acceptable carrier. In one embodiment, the chemotherapeutic agent is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of (and a pharmaceutical composition for) treating in a mammal a disease or condition selected from lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system, (e.g., primary CNS lymphoma, spinal axis tumors, brain stem gliomas or pituitary adenomas), Barrett's esophagus (pre-malignant syndrome), neoplastic cutaneous disease, psoriasis, mycoses fungoides, benign prostatic hypertrophy, human papilloma virus (HPV), and restinosis which comprises administering a compound of formula 1 or 2, or a pharmaceutically acceptable salt, solvate or prodrug thereof, that is effective in inhibiting farnesyl protein transferase or is otherwise effective in treating said disease or condition.

This invention also relates to a method of (and to a pharmaceutical composition for) treating abnormal cell growth in a mammal which comprise an amount of a compound of formula 1 or 2, or a pharmaceutically acceptable salt, solvate or prodrug thereof, and an amount of one or more substances selected from anti-angiogenesis agents, signal transduction inhibitors, and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 or 2 in the methods and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

® 3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and ® 3-[4-(4-fluoro-phenoxy)-benzenesulfonylamino]-tetrahydro-furan-3-carboxylic acid hydroxyamide;

and pharmaceutically acceptable salts, solvates and prodrugs of said compounds.

The compounds of formula 1 and 2, and the pharmaceutically acceptable salts, solvates and prodrugs thereof, can also be used in combination with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, New Jersey, USA), VRCTC-310 (Ventech Research) and EGF fusion toxin (Seragen Inc. of Hopkinton, Mass.).

VEGF inhibitors, for example SU-5416 and SU-6668 (Sugen Inc. of South San Francisco, Calif., USA), can also be combined with a compound of formula 1 or 2. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound of formula 1 or 2. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

A compound of formula 1 or 2 may also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application No. 60/113,647 (filed Dec. 23, 1998) which is herein incorporated by reference in its entirety.

The term "abnormal cell growth", as used herein, unless otherwise indicated, means cell growth that is independent of normal regulatory mechanisms (e.g., loss of contact inhibition). This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; and (3) benign and malignant cells of proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase. The terms "abnormal cell growth" and "proliferative" disorder or condition, as used herein, refer to the same conditions, that is, in particular, cancer or benign conditions such as psoriasis.

The term "treating", as used herein, unless otherwise indicated, means reversing, alleviating, inhibiting the progress of, or preventing the disorder or condition (i.e., abnormal cell growth) to which such term applies, or one or more symptoms of such disorder or condition. The term "treatment", as used herein, refers to the act of treating, as "treating" is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, means saturated monovalent hydrocarbon radicals having straight or branched moieties. Examples of alkyl groups include, but are not limited to, methyl, ethyl, propyl, isopropyl, and t-butyl.

The term "cycloalkyl", as used herein, unless otherwise indicated, means cyclic alkyl moieties wherein alkyl is as defined above. Multicyclic, such as bicyclic and tricyclic, groups are included in this definition.

The term "alkenyl", as used herein, unless otherwise indicated, means alkyl moieties having at least one carbon-carbon double bond wherein alkyl is as defined above.

The term "alkynyl", as used herein, unless otherwise indicated, means alkyl moieties having at least one carbon-carbon triple bond wherein alkyl is as defined above. Examples of alkynyl groups include, but are no limited to, ethynyl and 2-propynyl.

The term "alkoxy", as used herein, unless otherwise indicated, means O-alkyl groups wherein alkyl is as defined above.

The term "aryl", as used herein, unless otherwise indicated, means an organic radical derived from an aromatic hydrocarbon by removal of one hydrogen, such as phenyl or naphthyl.

The term "4 to 10 membered heterocyclic", as used herein, unless otherwise indicated, means aromatic and non-aromatic heterocyclic groups (including saturated or partially unsaturated heterocyclic groups) containing one or more heteroatoms each selected from O, S and N, wherein each ring of a heterocyclic group has from 4 to 10 atoms. Non-aromatic heterocyclic groups may include rings having only 4 atoms, but aromatic heterocyclic rings must have at least 5 atoms. Heterocyclic groups of this invention, unless otherwise indicated, may contain one ring or more than one ring, i.e. they may be monocyclic or multicyclic, for example bicyclic (which may comprise non-aromatic or aromatic rings, or both a non-aromatic ring and an aromatic ring). Preferably, bicyclic heterocyclic groups of this invention contain 6–9 members in their ring systems. Monocyclic heterocyclic groups of this invention preferably contain 5 or 6 members. Aromatic multicyclic heterocyclic groups include benzo-fused ring systems. The heterocyclic groups of this invention can also include ring systems substituted with one or two oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, piperidinyl, 1,2,3,6-tetrahydropyridinyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl.

The phrase "pharmaceutically acceptable salt(s)", as used herein, unless otherwise indicated, means salts of acidic or basic groups which may be present in the compounds of formula 1 and 2. The compounds of formula 1 and 2 that are basic in nature are capable of forming a wide variety of salts with various inorganic and organic acids. The acids that may be used to prepare pharmaceutically acceptable acid addition salts of such basic compounds of formula 1 and 2 are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts. Since a single compound of the present invention may include more than one acidic or basic moieties, the compounds of the present invention may include mono, di or tri-salts in a single compound.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Where $R^{11}$ and $R^{12}$ are as $(CR^{11}R^{12})_q$ or $(CR^{11}R^{12})_t$, each $R^{11}$ and $R^{12}$ is defined for each iteration of q or t in excess of 1. This means, for instance, that where q or t is 2, alkylene moieties of the type —$CH_2CH(CH_3)$—, and other asymmetrically branched groups, are included.

Certain compounds of formula 1 and 2 may have asymmetric centers and therefore exist in different isomeric forms. All optical isomers and stereoisomers of the compounds of formula 1 and 2, and mixtures thereof, are considered to be within the scope of the invention. With respect to the compounds of formula 1 and 2, the invention includes the use of a racemate, one or more enantiomeric forms, one or more diastereomeric forms, or mixtures thereof. The compounds of formula 1 and 2 may also exist as tautomers. This invention relates to the use of all such tautomers and mixtures thereof.

The subject invention also includes isotopically-labelled compounds, which are identical to those recited in formula 1 or 2, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{35}S$, $^{18}F$, and 36Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula 1 and 2 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating proliferative disorders, or abnormal cell growth, by administering prodrugs of compounds of the formula 1 or 2. Compounds of formula 1 and 2 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1 and 2. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

DETAILED DESCRIPTION OF THE INVENTION

In the following Schemes and Examples, "Et" represents an ethyl moiety, and "Me" represents a methyl moiety. Hence, for example, "OEt" means ethanol. Also, "THF" means tetrahydrofuran, and "DMF" means dimethylformamide.

The compounds of formulas 1 and 2 may be prepared as described below.

With reference to Scheme 1 below, the compounds of formula 1 may be prepared by hydrolysing an intermediate ether of formula 2', wherein R is $C_1$–$C_6$ alkyl, according to methods familiar to those skilled in the art, such as by stirring the intermediate of formula 2' in an aqueous acid solution. An appropriate acid is, for example, hydrochloric acid. The resulting quinolinone of formula 1 wherein $R^1$ is hydrogen may be transformed into a quinolinone wherein $R^1$ has a meaning as defined above apart from hydrogen by N-alkylation methods familiar to those skilled in the art.

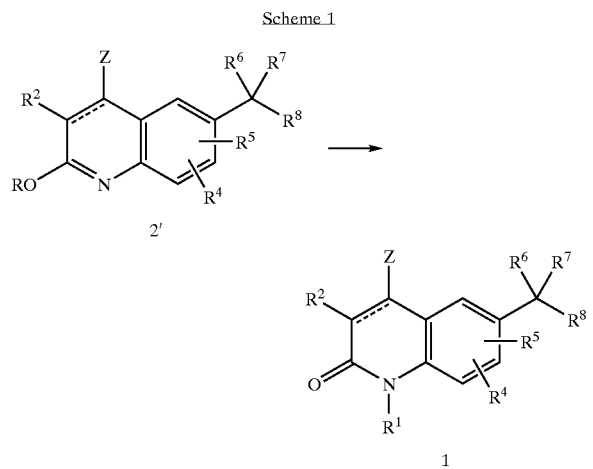

With reference to Scheme 2 below, the intermediate of formula 2', referred to above, may be prepared by reacting an intermediate of formula 10, wherein W is an appropriate leaving group, such as halo, with an intermediate ketone of formula 11. This reaction is done by converting the intermediate of formula 10 into a organometallic compound, by stirring it with a strong base such as butyl lithium, and subsequently adding the intermediate ketone of formula 11. Although this reaction gives at first instance a hydroxy derivative ($R^6$ is hydroxy), said hydroxy derivative can be converted into other intermediates wherein $R^6$ has another definition by performing functional group transformations familiar to those skilled in the art.

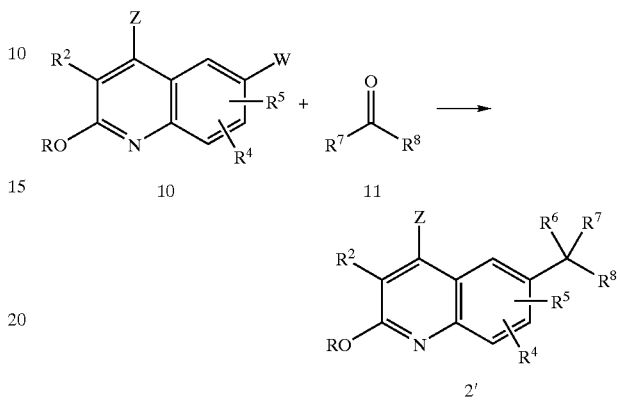

With reference to Scheme 3 below, compounds of formula 36 can be prepared from intermediate 23. Intermediate of formula 23 can be synthesized by reacting an intermediate of formula 34 with an intermediate of formula 22, wherein W is an appropriate leaving group, such as halo, with an intermediate amide of formula 22. This reaction requires the presence of a suitable base, such as n-butyl lithium, in an appropriate solvent, such as diethyl ether at a temperature of from about −78° C. to about zero degrees Celsius. Subsequent treatment of the resulting intermediate of formula 23 with a suitable reagent, such as $R^2CH_2COCl$ or $R^2CH_2COOC_2H_5$, wherein $R^2$ is as defined above, yields either directly a compound of formula 36 or an intermediate which can be converted to a compound of formula 36 by treatment with a base, such as potassium tert-butoxide. The intermediate of formula 36 can be converted to intermediate of formula 10 by stirring it with an O-alkylation reagent, such as trimethyloxonium tetrafluoroborate ($BF_4OMe_3$) for a period of time, typically 4 to 15 hours, and subsequently adding a strong base such as sodium hydroxide in aqueous.

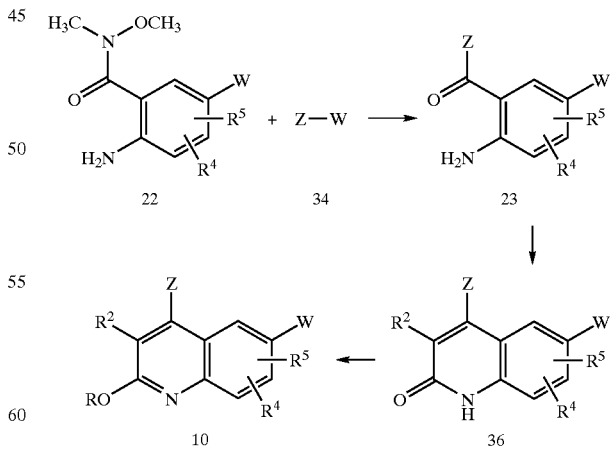

With reference to Scheme 4 below, compounds of formula 1 wherein $R^6$ is a radical of formula $-NR^{10}OR^{11}$ wherein $R^{10}$ and $R^{11}$ are as described above (said compounds are represented below by formula 1(g)), may be prepared by reacting an intermediate of formula 13, wherein W is an appropriate leaving group, such as halo, with a reagent of formula 14. Said reaction may be performed by stirring the reactants in an appropriate solvent, such as tetrahydrofuran.

Scheme 4

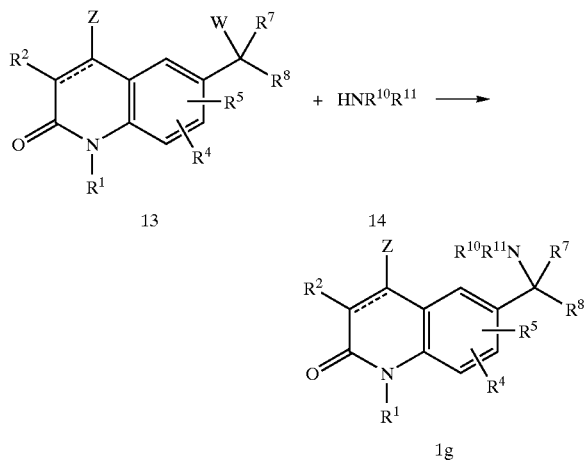

Compounds of formula 1(g), or other embodiments of formula 1, wherein the dotted line represents a bond can be converted into compounds wherein the dotted line does not represent a bond by hydrogenation methods familiar to those skilled in the art. Compounds wherein the dotted line does not represent a bond may be converted into compounds wherein the dotted line represents a bond by oxidation methods familiar to those skilled in the art.

With reference to Scheme 5 below, compounds of formula 1 wherein $R^6$ is hydroxy (said compounds being represented by formula 1b) may be converted into compounds of formula 1c, wherein $R^{10}$ has the meaning described above except it is not hydrogen, by methods known to those skilled in the art, including O-alkylation or O-acylation reactions; such as by reacting the compound of formula 1b with an alkylating reagent such as $R^{10}$—W, wherein $R^{10}$ is as described above, in appropriate conditions, such as in a dipolar aprotic solvent, such as DMF, in the presence of a base, such as sodium hydride. W is a suitable leaving group, such as a halo group or a sulfonyl group.

Scheme 5

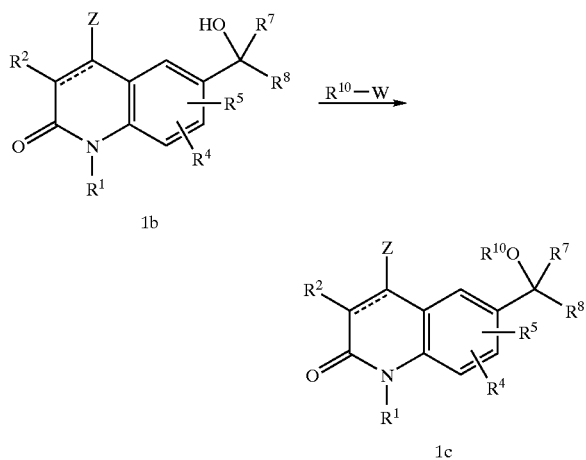

As an alternative to the above reaction procedure, compounds of formula 1c may also be prepared by reacting a compound of formula 1b with a reagent of formula $R^{10}$—OH, wherein $R^{10}$ is as described above, in acidic medium.

Compounds of formula 1b may also be converted into compounds of formula 1g, wherein $R^{10}$ is hydrogen and $R^{11}$ is replaced with $C_1$–$C_6$ alkylcarbonyl, by reacting compounds of formula 1b in acidic medium, such as sulfuric acid, with $C_1$–$C_6$ alkyl-CN in a Ritter-type reaction. Further, compounds of formula 1b may also be converted into compounds of formula 1g, wherein $R^{10}$ and $R^{11}$ are hydrogen, by reacting a compound of formula 1b with ammonium acetate and subsequent treatment with $NH_3$(aq.).

With reference to Scheme 6 below, compounds of formula 1b, referred to above, may also be converted into compounds of formula 1d, wherein $R^6$ is hydrogen, by submitting a compound of formula 1b to appropriate reducing conditions, such as stirring in trifluoroacetic acid in the presence of an appropriate reducing agent, such as sodium borohydride, or, alternatively, stirring the compound of formula 1b in acetic acid in the presence of formamide. Further, the compound of formula 1d wherein $R^6$ is hydrogen may be converted into a compound of formula 1e wherein $R^6$ is $C_1$–$C_{10}$ alkyl by reacting the compound of formula 1d with a reagent of formula 5, wherein W is an appropriate leaving group, in an appropriate solvent, such as diglyme, in the presence of a base, such as potassium tert-butoxide.

Scheme 6

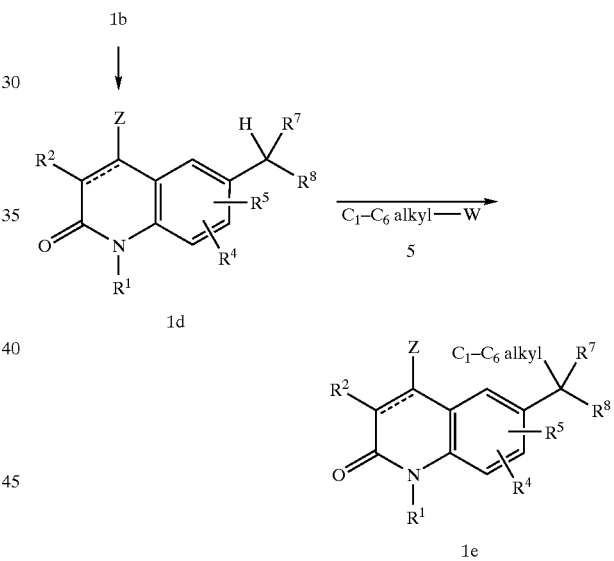

The substituents of the compounds of formulas 1 and 2 may be converted to other substituents falling within the scope of formulas 1 and 2 via reactions or functional group transformations familiar to those skilled in the art. A number of such transformations are already described above. Other examples are hydrolysis of carboxylic esters to the corresponding carboxylic acid or alcohol; hydrolysis of amides to the corresponding carboxylic acids or amines; hydrolysis of nitrites to the corresponding amides; amino groups on imidazole or phenyl moieties may be replaced by hydrogen by diazotation reactions familiar to those skilled in the art, and subsequent replacement of the diazo-group by hydrogen; alcohols may be converted into esters and ethers; primary amines may be converted into secondary or tertiary amines; double bonds may be hydrogenated to the corresponding single bond.

With reference to Scheme 7 below, intermediates of formula 29 may be prepared by reacting an intermediate of formula 10 with an intermediate of formula 28, or a functional derivative thereof, under appropriate conditions. This reaction is done by converting the intermediate of formula 10 into an organometallic compound, by stirring it with a strong base such as butyl lithium, and subsequently adding the intermediate amide of formula 28.

Scheme 7

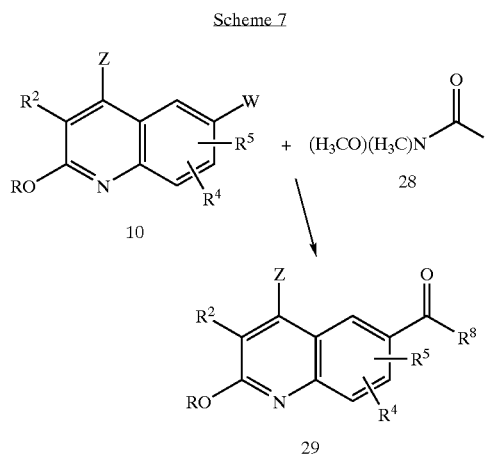

With reference to Scheme 8 below, the compound of formula 30 can be prepared by hydrolysing an intermediate formula 29, wherein R is $C_1$–$C_6$ alkyl, according to methods familiar to those skilled in the art, such as by stirring the intermediate of formula 29 in an aqueous acid solution or in an organic solvent with the presence of a Lewis acid. An appropriate acid is, for example, hydrochloric acid. An appropriate Lewis acid and the solvent are, for example, iodotrimethylsilane and dicholoromethane. The resulting quinolinone of formula 30 wherein $R^1$ is hydrogen may be transformed into a quinolinone wherein $R^1$ has a meaning as defined above apart from hydrogen by N-alkylation methods familiar to those skilled in the art.

Scheme 8

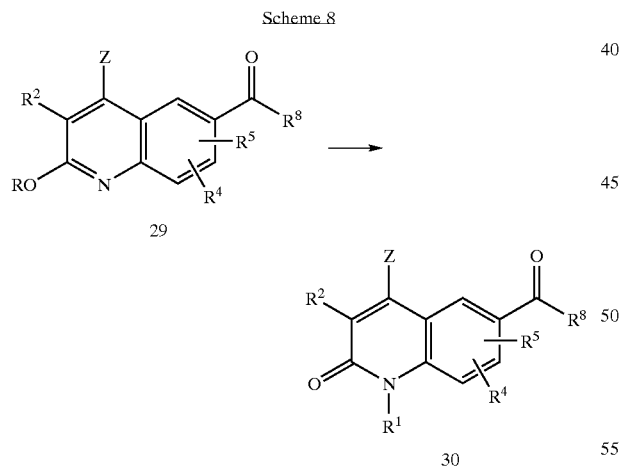

With reference to Scheme 9 below, the compound of formula 26 can be prepared by reacting a compound of formula 25 with an intermediate of formula 27 where $R^{12}$ is H or phenyl. This reaction requires the presence of a suitable base, such as tert-butyl lithium (when $R^{12}$=H) or lithium 2,2,6,6,-tetramethylpiperidine (when $R^{12}$=phenyl), in an appropriate solvent, such as THF. The —$SR^{12}$ group can be reductively removed from the compound of formula 26 with RANEY™ nickel or oxidatively with nitric acid or aqueous hydrogen peroxide in acetic acid.

Scheme 9

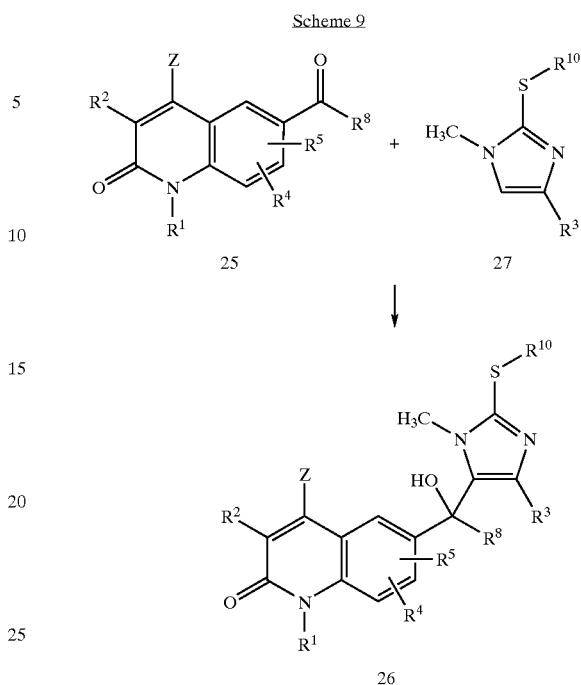

With reference to Scheme 10 below, compounds of formula 1 wherein $R^6$ is a radical of formula —$NR^{10}R^{11}$ (said compound are represented below by formula 1), may be prepared by stirring the compound of formula 2 with thionyl chloride neat or in a solvent such as toluene at a temperature of 60° C. and above. Subsequent treatment with a reagent of formula 14 at a temperature of –78° C. to 0 degrees C. yields the quinolinone of formula 1 wherein $R^1$ is hydrogen. Compounds of formula 1 wherein $R^1$ is hydrogen may be transformed into compounds of formula 1 wherein $R^1$ has a meaning as defined above apart from hydrogen by N-alkylation methods familiar to those skilled in the art.

Scheme 10

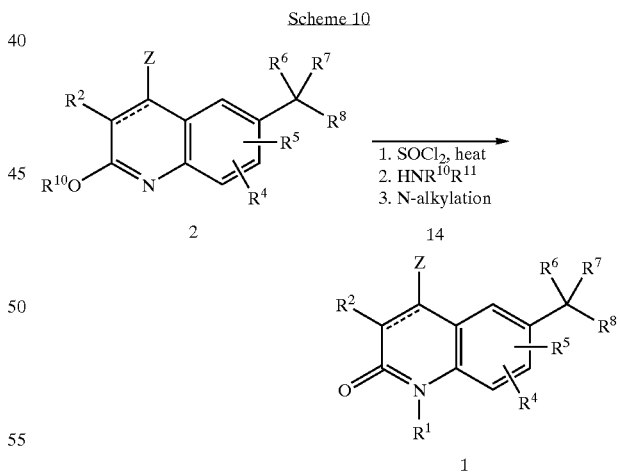

With reference to Scheme 11, intermediates of formula 11a, which are compounds of formula 11 wherein $R^7$ is a substituted imidazole, may be prepared by reacting an intermediate of formula 28 with an intermediate of formula 33 where $R^{14}$,$R^{15}$, $R^{16}$ are $C_1$–$C_6$ alkyl or phenyl to generate an intermediate of formula 32. This reaction requires the presence of a suitable base, such as n-butyl lithium, in an appropriate solvent, such as THF. The intermediate of formula 32 is reacted with acetic acid or a fluoride reagent such as tetrabutylammonia fluoride (TBAF) in a solvent such as tetrahydrofuran to obtain the compound of formula 11a. Alternatively, the compound of formula 11a can be prepared by reacting a compound of formula 28 with an intermediate of formula 27 where $R^{10}$ is H or phenyl. This reaction requires the presence of a suitable base, such as tert-butyl lithium (when $R^{10}$=H) or lithium 2,2,6,6,-tetramethylpiperidine (when $R^{10}$=phenyl), in an appropriate solvent, such as THF. The —$SR^{10}$ group can be reductively removed from the compound of formula 31 with RANEY™ nickel or oxidatively with nitric acid or aqueous hydrogen peroxide in acetic acid.

with various inorganic and organic acids. Although such salts must be pharmaceutically acceptable for administration to animals, it is often desirable in practice to initially isolate the compounds of formulas 1 and 2 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the

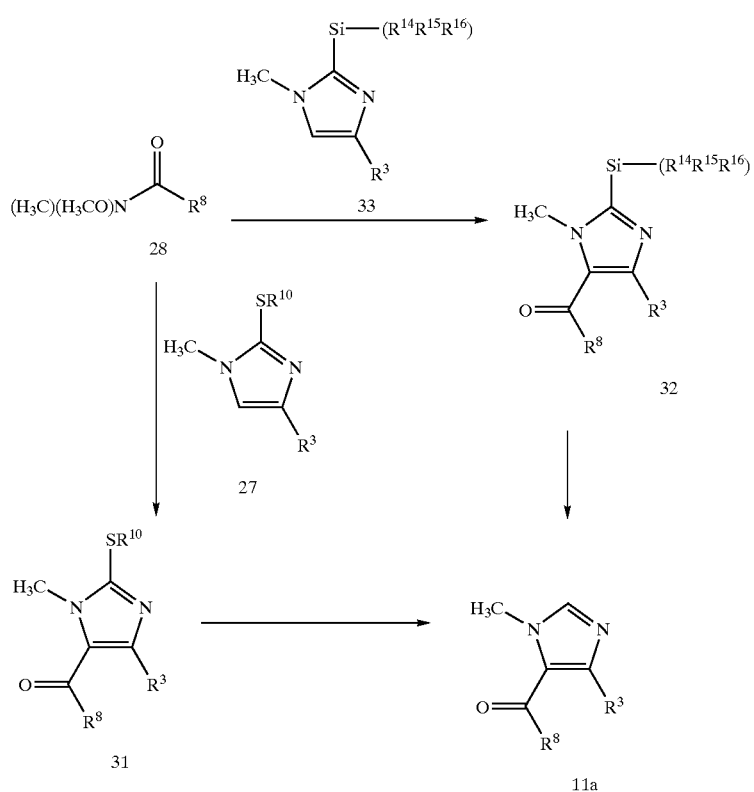

Scheme 11

The compounds of formulas 1 and 2 as prepared in the above processes are generally racemic mixtures of enantiomers which can be separated from one another following resolution procedures familiar to those skilled in the art. The racemic compounds of formulas 1 and 2 may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomerics forms of the compounds of formulas 1 and 2 involves liquid chromatography using a chiral stationary phase. Said pure stereochemically isomeric forms may also be derived from the corresponding pure stereochemically isomeric forms of the appropriate starting materials, provided that the reaction occurs sterospecifically. Preferably if a specific stereoisomer is desired, said compound will be synthesized by stereospecfic methods of preparation. These methods will advantageously employ enantiomerically pure starting materials.

The compounds of formulas 1 and 2 that are basic in nature are capable of forming a wide variety of different salts chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Cationic salts of the compounds of formulas 1 and 2 are similarly prepared except through reaction of a carboxy group with an appropriate cationic salt reagent, such as sodium, potassium, calcium, magnesium, ammonium, N,N'-dibenzylethylenediamine, N-methylglucamine (meglumine), ethanolamine, tromethamine, or diethanolamine.

Patients that can be treated with a compound of formulas 1 and 2, or a pharmaceutically acceptable salt or solvate thereof, according to the methods of this invention include, for example, patients that have been diagnosed as having lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem gliomas or pituitary adenomas), neoplastic cutaneous diseases (e.g. psoriasis, mycoses fungoides), or Barrett's esophagus (pre-malignant syndrome).

The compounds of formulas 1 and 2 may be used in a palliative neo-adjuvant/adjuvant therapy in alleviating the symptoms associated with the diseases recited in the preceding paragraph as well as the symptoms associated with abnormal cell growth. Such therapy can be a monotherapy or can be in a combination with chemotherapy and/or immunotherapy.

Patients that can be treated according to the methods of this invention also include patients suffering from abnormal cell growth, as defined above.

The compounds of formulas 1 and 2, and their pharmaceutically acceptable salts and solvates (hereinafter referred to, collectively, as "the therapeutic compounds") can be administered orally, transdermally (e.g., through the use of a patch), parenterally or topically. Oral administration is preferred. In general, compounds of the formulas 1 and 2, and their pharmaceutically acceptable salts and solvates are most desirably administered in dosages ranging from about 1.0 mg up to about 500 mg per day, preferably from about 1 to about 100 mg per day in single or divided (i.e., multiple) doses. The therapeutic compounds will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art.

Additionally, it is also possible to administer the therapeutic compounds topically and this may preferably be done by way of creams, jellies, gels, pastes, ointments and the like, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

For the combination therapies and pharmaceutical compositions described herein, the effective amounts of the compound of the invention and of the chemotherapeutic or other agent useful for inhibiting abnormal cell growth (e.g., other antiproliferative agent, anti-agiogenic, signal transduction inhibitor or immune-system enhancer) can be determined by those of ordinary skill in the art, based on the effective amounts for the compound described herein and those known or described for the chemotherapeutic or other agent. The formulations and routes of administration for such therapies and compositions can be based on the information described herein for compositions and therapies comprising the compound of the invention as the sole active agent and on information provided for the chemotherapeutic or other agent in combination therewith.

The compounds of formulas 1 and 2 exhibit activity as Ras farnesylation inhibitors and are useful in the treatment of cancer and the inhibition of abnormal cell growth in mammals, including humans. The activity of the compounds of formulas 1 and 2 as Ras farnesylation inhibitors may be determined by their ability, relative to a control, to inhibit Ras farnesyl transferase in vitro. An example of one such procedure is described below.

A crude preparation of human farnesyl transferase (FTase) comprising the cytosolic fraction of homogenized brain tissue is used for screening compounds in a 96-well assay format. The cytosolic fraction is prepared by homogenizing approximately 40 grams of fresh tissue in 100 ml of sucrose/MgCl$_2$/EDTA buffer (using a Dounce homogenizer; 10–15 strokes), centrifuging the homogenates at 1000 g for 10 minutes at 4° C., re-centrifuging the supernatant at 17,000 g for 15 minutes at 4° C., and then collecting the resulting supernatant. This supernatant is diluted to contain a final concentration of 50 mM Tris HCl (pH 7.5), 5 mM DTT, 0.2 M KCl, 20 µM ZnCl$_2$, 1 mM PMSF and re-centrifuged at 178,000 g for 90 minutes at 4° C. The supernatant, termed "crude FTase" is assayed for protein concentration, aliquoted, and stored at −70° C.

The assay used to measure in vitro inhibition of human FTase is a modification of the method described by Amersham LifeScience for using their Farnesyl transferase (3H) Scintillation Proximity Assay (SPA) kit (TRKQ 7010). FTase enzyme activity is determined in a volume of 100 µl containing 50 mM N-(2-hydroxy ethyl) piperazine-N-(2-ethane sulfonic acid) (HEPES), pH 7.5, 30 mM MgCl$_2$, 20 mM KCl, 25 mM Na$_2$HPO$_4$, 5 mM dithiothreitol (DTT), 0.01% Triton X-100, 5% dimethyl sulfoxide (DMSO), 20 mg of crude FTase, 0.12 mM [3H]-farnesyl pyrophosphate ([3H]-FPP; 36000 dpm/pmole, Amersham LifeScience), and 0.2 µM of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 150 µl of steptavidin-coated SPA beads (TRKQ 7010) per well and incubating the reaction mixture for 30 minutes at room temperature. The amount of radioactivity bound to the SPA beads is determined using a MicroBeta 1450 plate counter. Under these assay conditions, the enzyme activity is linear with respect to the concentrations of the prenyl group acceptor, Bt-KTKCVIS, and crude FTase, and inhibition of Bt-KTKCVIS interaction with FTase can be detected. The enzyme activity is saturating with respect to the prenyl donor, FPP. The assay reaction time is also in the linear range.

The test compounds are routinely dissolved in 100% DMSO. Inhibition of farnesyl transferase activity is determined by calculating percent incorporation of tritiated-farnesyl in the presence of the test compound versus its incorporation in control wells (absence of inhibitor). IC$_{50}$ values, that is, the concentration required to produce half maximal farnesylation of Bt-KTKCVIS, is determined from the dose-responses obtained.

All of the title compounds of formulas 1 and 2 in the following Examples were assayed for their ability to inhibit the activity of human farnesyl transferase in vitro using the assay described above, and were found to have IC$_{50}$ values for inhibiting farnesylation of the biotinylated KTKCVIS-peptide of about less than or equal to 500 nM.

The following Examples are provided to illustrate aspects of the subject invention. They are not intended, nor should they be construed, to limit the invention as more fully described herein and set forth in the claims.

EXAMPLE 1

(4-Chloro-phenyl)-[2-methoxy-4-(5-methyl-thiophen-2-yl)-quinolin-6-yl]-(3-methyl-3H-imidazol-4-yl)-methanol 1A. (2-Amino-5-bromo-phenyl)-(5-methyl-thiophen-2-yl)-methanone A solution of 2-amino-5-bromo-N-methoxy-N-methyl-benzamide (0.37 g, 1.43 mmol) and 2-bromo-5-methyl-thiophene (0.254 mg, 1.43 mmol) in anhydrous ether (8 ml) was degassed for 10 minutes before cooling to −78° C. n-Butyl lithium (2.5 M in hexane, 1.14 ml, 2.86 mmol) was added dropwise. The resulting bright yellow solution was stirred at −78° C. for one hour and 0° C. for 20 minutes, after which time it was quenched with 3 ml of saturated aqueous solution of ammonium chloride. It was partitioned between ethyl acetate and 10% aqueous solution of potassium carbonate. The organic layer was washed with brine, dried over MgSO$_4$ and concentrated under vacuum to give the crude product. It was purified via chromatography with 20% ethyl acetate in hexane as the eluent to afford 2-amino-5-bromo-phenyl)-(5-methyl-thiophen-2-yl)-methanone (0.161 g, 0.544 mmol, 38% yield).

Cl-MS: m/z 295.8, 293.8 [M+1].

1B. 6-Bromo-4-(5-methyl-thiophen-2-yl)-1H-quinolin-2-one

2-Amino-5-bromo-phenyl)-(5-methyl-thiophen-2-yl)-methanone (3.28 g, 11.08 mmol) was suspended in anhydrous toluene (20 ml) under an atmosphere of dry N$_2$. To this solution was added sequentially acetic anhydride (Ac$_2$O, 3.91 ml, 41.44 mmol), triethylamine (NEt$_3$, 11.53 ml, 82.88 mmol) and 4-dimethylaminopyridine (DMAP, 1.27 g, 10.36 mmol). The reaction mixture was then heated to reflux and stirred at this temperature for 20 hours. The reaction mixture was cooled to ambient temperature and the precipitate was collected via suction filtration. The solid was washed with ethyl ether (Et$_2$O) and dried under vacuum to give 6-bromo-4-(5-methyl-thiophen-2-yl)-1H-quinolin-2-one as an off-white solid (0.929 g, 26% yield).

Cl-MS: m/z 319.8, 321.8 [M+1].

1C. 6-Bromo-2-methoxy-4-(5-methyl-thiophen-2-yl)-quinoline

The title compound of example 1B (0.929 g, 2.90 mmol) was suspended in DCM (dichloromethane)(3 ml) under an atmosphere of dry N$_2$. To this suspension, was added trimethyloxonium tetrafluoroborate (BF4OMe3, 0.54 g, 3.63 mmol). The reaction mixture was stirred at ambient temperature for 3 hours. It was then cooled at 0° C. and NaHCO3 (0.94 g) in water (4 ml) was added. The reaction mixture was allowed to warm to room temperature and stirred for one hours after which time it was partitioned between DCM and water. The DCM layer was washed with brine, dried over MgSO$_4$ and concentrated under vacuum to give the crude product. It was purified via chromatography with chloroform as the eluent to afford 6-bromo-2-methoxy-4-(5-methyl-thiophen-2-yl)-quinoline as an off-white solid (0.7 g, 2.10 mmol, 72.5% yield).

Cl-MS: m/z 333.8, 335.8 [M+1].

1D (4-Chloro-phenyl)-[2-methoxy-4-(5-methyl-thiophen-2-yl)-quinolin-6-yl]-(3-methyl-3H-imidazol-4-yl)-methanol To a solution of the title compound of example 1C (0.200 g, 0.598 mmol) in THF (1.5 ml) was added n-buthyl lithium (2.5 M in hexane, 0.251 ml, 0.628 mmol) dropwise at −780° C. under an atmosphere of dry N$_2$. After stirring at −780° C. for 15 minutes, a solution of (4-chloro-phenyl)-(3-methyl-3H-imidazol-4-yl)-methanone (0.158 g, 0.718 mmol) in THF (1.0 ml) was added. The reaction mixture was allowed to warm to ambient temperature and stirred for 15 hours. To the mixture was added a saturated aqueous solution of ammonium chloride at 0° C. THF was removed from the resulting heterogeneous solution. The aqueous mixture was partitioned between 10% aqueous $K_2CO_3$ and ethyl acetate. The organic layer was washed with brine, dried over $MgSO_4$ and concentrated under vacuum to yield the crude product. It was chromatographed on silica gel with gel with MeOH—$CHCl_3$—NH4 (1:99:0.1) as eluents to afford the title compound of Example 1 as a white solid (0.140 g, 0.294 mmol, 49% yield).

Cl-MS: m/z 475.9, 477.9 [M+1].

EXAMPLE 2

6-[(4-Chloro-phenyl)-hydroxy-(3-methyl-3H-imidazol-4-yl)-methyl]-4-(5-methyl-thiophen-2-yl)-1H-quinolin-2-one To a solution of (4-Chloro-phenyl)-[2-methoxy-4-(5-methyl-thiophen-2-yl)-quinolin-6-yl]-(3-methyl-3H-imidazol-4-yl)-methanol (0.137 g, 0.288 mmol) in THF (3.2 ml) was added concentrated hydrogen chloride (HCl, 0.314 ml) dropwise. The mixture was heated at 60° C. for 24 hours. After cooling to room temperature, THF was removed. The aqueous solution was adjusted to pH=~9 with 40% aqueous NaOH. The yellow solid was precipitated out. After filtration and washed with ethylacetae obtained 6-[(4-chloro-phenyl)-hydroxy-(3-methyl-3H-imidazol-4-yl)-methyl]-4-(5-methyl-thiophen-2-yl)-1H-quinolin-2-one (0.115 g, 0.248 mmol, 86%yield).

Cl-MS: m/z 462.3, 464.3 [M+1].

EXAMPLE 3

6-[(4-Chloro-phenyl)-hydroxy-(3-methyl-3H-imidazol-4-yl)-methyl]-1-methyl-4-(5-methyl-thiophen-2-yl)-1H-quinolin-2-one To a solution of 6-[(4-chloro-phenyl)-hydroxy-(3-methyl-3H-imidazol-4-yl)-methyl]-4-(5-methyl-thiophen-2-yl)-1H-quinolin-2-one (115 mg, 0.248 mmol) in THF (6.6 ml) was added a 40% aqueous NaOH (3.3 ml), benzyltriethylammonium chloride (28 mg. 0.124 mmol) and a solution of methyl iodide (0.017 ml, 0.273 mmol) in THF (0.05 ml). The reaction mixture was stirred at ambient temperature for 1.5 hours after which time it was partitioned between ethyl acetate and 10% aqueous potassium carbonate. The organic layer was washed with brine, dried over $MgSO_4$ and concentrated under vacuum to give the crude product. It was chromatographed on silica gel with MeOH—$CHCl_3$—$NH_4$ (1:99:0.1) as eluents to afford the title compound as a white solid (68 mg, 0.143 mmol, 58% yield).

Cl-MS: m/z 475.9, 477.9 [M+1].

EXAMPLE 4

6-[Amino-(4-chloro-phenyl)-(3-methyl-3H-imidazol-4-yl)-methyl]-1-methyl-4-(5-methyl-thiophen-2-yl)-1H-quinolin-2-one To a solution of 6-[(4-chloro-phenyl)-hydroxy-(3-methyl-3H-imidazol-4-yl)-methyl]-1-methyl-4-(5-methyl-thiophen-2-yl)-1H-quinolin-2-one (63 mg, 0.132 mmol) in toluene (1 ml) was added thionyl chloride ($SOCl_2$, 0.097 ml, 1.32 mmol). The reaction mixture was heated to reflux for 2 hours. Thiony chloride was removed under reduced pressure. The crude chloride was taken up in toluene and concentrated under vacuum. The resulting solid was dissolved in THF (5 mL) and to this solution was bubbled ammonia gas ($NH_3$) for 10 minutes at −78° C. The excess $NH_3$ was removed via bubble $N_2$ at −30° C. After removal of THF, the product mixture was partitioned between ethyl acetate and 10% aqueous potassium carbonate. The organic layer was washed, dried over $MgSO_4$ and concentrated under vacuum to give the crude product. It was chromatographed on silica gel with $CHCl_3$ then MeOH—$CHCl_3$—$NH_4OH$ (1:99:0.1) as eluents to afford the titled compound as an off-white solid (31 mg, 0.065 mmol, 49% yield).

Cl-MS: m/z 475.2, 477.4 [M+1].

EXAMPLE 5

6-[(4-Chloro-phenyl)-hydroxy-(3-methyl-3H-imidazol-4-yl)-methyl]-4-(-chloro-thiophen-2-yl)-1-methyl-1H-quinolin-2-one 5A. (2-Amino-5-bromo-phenyl)-(5-chloro-thiophen-2-yl)-methanone According to the procedure described in example 1A, reaction of 2-amino-5-bromo-N-methoxy-N-methyl-benzamide (5.00 g, 19.2 mmol) and 2-bromo-5-chloro-thiophene (27.0 g, 1.40 mmol) afforded 2-amino-5-bromo-phenyl)-(5-chloro-thiophen-2-yl)-methanone (3.96 g, 64% yield).

Cl-MS: m/z 315.8, 317.8[M+1].

5B. 6-Bromo-4-(5-chloro-thiophen-2-yl)-1H-quinolin-2-one

The same procedure was used as that in example 1B, except that 2-amino-5-bromo-phenyl)-(5-chloro-thiophen-2-yl)-methanone (3.97 g, 12.5 mmol) was used in the place of 2-amino-5-bromo-phenyl)-(5-methyl-thiophen-2-yl)-methanone, to give title compound as an off-white solid (3.69 g, 10.8 mmol, 87% yield).

$^1$H NMR (CDCl3) δ 12.00 (s, 1H), 7.80 (d, 1H, J=2.0 Hz), 7.39 (dd, 1H, J=8.81, 2.0 Hz), 7.69 (d, 1H, J=2.0 Hz), 7.36 (d, 1H, J=3.94 Hz), 7.31 (d, 1H, J=8.81 Hz), 7.28 (d, 1H), J=3.94 Hz), 7.28 (d, 1H, J=3.94 Hz), 6.56 (s, 1H).

5C. 6-Bromo-2-methoxy-4-(5-chloro-thiophen-2-yl)-quinoline

The same procedure was used as that in example 1C, except that 6-bromo-4-(5-chloro-thiophen-2-yl)-1H-quinolin-2-one (0.536 g, 1.57 mmol) was used in the place of 6-bromo-4-(5-methyl-thiophen-2-yl)-1H-quinolin-2-one, to give title compound as a white solid (0.257 g, 0.724 mmol, 46% yield).

Cl-MS: m/z 354.0, 356.0 [M+1].

5D. (4-Chloro-phenyl)-[2-methoxy-4-(5-chloro-thiophen-2-yl)-quinolin-6-yl]-(3-methyl-3H-imidazol-4-yl)-methanol The same procedure was used as that in example 1D, except that 6-bromo-2-methoxy-4-(5-chloro-thiophen-2-yl)-quinoline (0.377 g, 1.06 mmol) was used in the place of 6-bromo-2-methoxy-4-(5-methyl-thiophen-2-yl)-quinoline, to give title compound as a white solid (0.284 g, 54% yield).

Cl-MS: m/z 496.1, 498.1 [M+1].

5E. 6-[(4-Chloro-phenyl)-hydroxy-(3-methyl-3H-imidazol-4-yl)-methyl]-4-(5-chloro-thiophen-2-yl)-1H-quinolin-2-one The same procedure was used as that in example 2, except that (4-chloro-phenyl)-[2-methoxy-4-(5-chloro-thiophen-2-yl)-quinolin-6-yl]-(3-methyl-3H-imidazol-4-yl)-methanol (0.194 g, 0.391 mmol) was used in the place (4-chloro-phenyl)-[2-methoxy-4-(5-methyl-thiophen-2-yl)-quinolin-6-yl]-(3-methyl-3H-imidazol-4-yl)-methanol, to give title compound as a white solid (0.178 g, 0.369 mmol, 94% yield).

5F. 6-[(4-Chloro-phenyl)-hydroxy-(3-methyl-3H-imidazol-yl)-methyl]4-(5-chloro-thiophen-2-yl)-1-methyl-1H-quinolin-2-one The same procedure was used as that in example 3, except that 6-[(4-chloro-phenyl)-hydroxy-(3-methyl-3H-imidazol-4-yl)-methyl]4-(5-chloro-thiophen-2-yl)-1H-quinolin-2-one (0.239 g, 0.481 mmol) was used in the place of 6-[(4-chloro-phenyl)-hydroxy-(3-methyl-3H-imidazol-4-yl)-methyl]-4-(5-methyl-thiophen-2-yl)-1H-quinolin-2-one, to give title compound as a white solid (0.078 g, 0.157 mmol, 33% yield).

Cl-MS: m/z 496.0, 498.0 [M+1].

Additional compounds that are part of the present invention and can be made according to one or more procedures described above are the following:

6-[Amino-(4-chloro-phenyl)-(3-methyl-3H-imidazol-4-yl)-methyl]-4-(5-chloro-thiazol-2-yl)-1-methyl-1H-quinolin-2-one 6-[Amino-(4-chloro-phenyl)-(3-methyl-3H-imidazol-4-yl)-methyl]-4-(5-chloro-pyridin-3-yl)-1-methyl-1H-quinolin-2-one 6-[Amino-(4-chloro-phenyl)-(3-methyl-3H-imidazol-4-yl)-methyl]-1-methyl-4-(6-methyl-pyridin-2-yl)-1H-quinolin-2-one 6-[(4-Chloro-phenyl)-hydroxy-(3-methyl-3H-imidazol-4-yl)-methyl]-4-(6-methyl-pyridin-2-yl)-1-methyl-1H-quinolin-2-one and the pharmaceutically acceptable salts, solvates, and prodrugs of the foregoing compounds.

What is claimed is:

1. A compound of the formula 1 or 2:

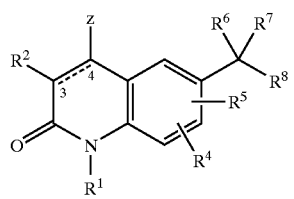

1

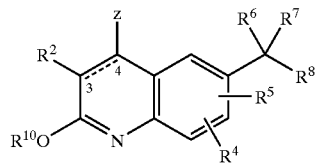

2 or a pharmaceutically acceptable salt, solvate or prodrug thereof wherein:

the dashed lines in formulas 1 and 2 indicate an optional second bond connecting C-3 and C-4 of the quinolin-2-one rings;

Z is a pyridine or a thiophene group optionally substituted with 1 to 4 $R^3$ substituents;

$R^1$ is selected from H, $C_1$–$C_{10}$ alkyl, —$(CR^{11}R^{12})_qC(O)R^{10}$, —$(CR^{11}R^{12})_qC(O)OR^9$, —$(CR^{11}R^{12})_qOR^{10}$, —$(CR^{11}R^{12})_qC(R^{11})(R^{12})SO_2R^9$, —$(CR^{11}R^{12})_t(C_3–C_{10}$ cycloalkyl), —$(CR^{11}R^{12})_t(C_6–C_{10}$ aryl), and —$(CR^{11}R^{12})_t(4$ to 10 membered heterocyclic), wherein each t is independently an integer from 0 to 5 and each q is independently an integer from 1 to 5; said cycloalkyl, aryl and heterocyclic $R^1$ groups are optionally fused to a $C_6$–$C_{10}$ aryl group, a $C_5$–$C_8$ saturated cyclic group, or a 4 to 10 membered heterocyclic group; and the foregoing $R^1$ groups, except H but including any optional fused rings referred to above, are optionally substituted with 1 to 4 $R^3$ groups;

$R^2$ is halo, cyano, —$C(O)OR^{10}$, or a group selected from the substituents provided in the definition of $R^{10}$;

each $R^3$, $R^4$ and $R^5$ is independently selected from H, $R^{10}$, $C_2$–$C_{10}$ alkenyl, $C_2$–$C_{10}$ alkynyl, halo, cyano, nitro, trifluoromethyl, trifluoromethoxy, azido, —$OR^{10}$, —$C(O)R^{10}$, —$C(O)OR^{10}$, —$NR^{11}C(O)OR^{10}$, —$OC(O)R^{10}$, —$NR^{11}SO_2R^{10}$, —$SO_2NR^{10}R^{11}$, —$NR^{11}C(O)R^{10}$, —$C(O)NR^{10}R^{11}$, —$NR^{10}R^{11}$, —$CH=NOR^{10}$, —$S(O)_jR^{10}$, —$(CR^{11}R^{12})_tC\equiv CR^{10}$, and —$C(R^{11}R^{12})_tC\equiv CR^{13}$, wherein each t is independently an integer from 0 to 5 and each j is independently an integer from 0 to 2; said alkyl, alkenyl, alkynyl, cycloalkyl, aryl, and heterocyclic moieties of the foregoing $R^3$, $R^4$, and $R^5$ groups are optionally substituted by 1 to 3 substituents independently selected from halo, cyano, nitro, trifluoromethyl, trifluoromethoxy, azido, —$NR^{11}SO_2(C_1$–$C_6$ alkyl), —$SO_2NR^{11}R^{12}$, —$C(O)R^{10}$, —$C(O)OR^{10}$, —$OC(O)R^{10}$, —$NR^{11}C(O)OR^{10}$, —$NR^{11}C(O)R^{10}$, —$C(O)NR^{11}R^{12}$, —$NR^{11}R^{12}$, hydroxy, $C_1$–$C_6$ alkoxy, $C_1$–$C_{10}$ alkyl, $C_2$–$C_{10}$ alkenyl, $C_2$–$C_{10}$ alkynyl, —$(CR^{11}R^{12})_t(C_6$–$C_{10}$ aryl), —$(CR^{11}R^{12})_t(C_3$–$C_{10}$ cycloalkyl), and —$(CR^{10}R^{10})_t(4$ to 10 membered heterocyclic), wherein each t is independently an integer from 0 to 5;

$R^6$ is H, cyano, —$(CR^{11}R^{12})_t(4$ to 10 membered heterocyclic) wherein t is an integer from 0 to 5, —$OR^{10}$, —$OC(O)R^{10}$, —$NR^{11}R^{11}$, —$NR^{11}C(O)H$, —$C(O)OR^{10}$, or —$SR^{10}$, wherein heterocyclic groups of said $R^6$ groups are optionally substituted by 1 to 4 $R^3$ groups;

$R^7$ is —$(CR^{11}R^{12})_t(imidazolyl)$ or —$(CR^{11}R^{12})_t(pyridinyl)$, wherein each t is an integer 0 to 5 and said imidazolyl and pyridinyl moieties are optionally substituted by up to 2 $R^3$ substituents;

$R^8$ is phenyl or an aromatic 4 to 10 membered heterocyclic group, and said $R^8$ group is optionally substituted by 1 to 4 $R^3$ substituents;

each $R^{10}$ is independently selected from H, $C_1$–$C_{10}$ alkyl, —$(CR^{11}R^{12})_t(C_3$–$C_{10}$ cycloalkyl), —$(CR^{11}R^{12})_t(C_6$–$C_{10}$ aryl), and —$(CR^{11}R^{12})_t(4$ to 10 membered heterocyclic); wherein each t is independently an integer from 0 to 5 and said cycloalkyl, aryl and heterocyclic $R^{10}$ groups are optionally fused to a $C_6$–$C_{10}$ aryl group, a $C_5$–$C_8$ saturated cyclic group, or a 4 to 10 membered heterocyclic group; and the foregoing $R^{10}$ substituents, except H but including any optional fused rings, are optionally substituted by 1 to 3 substituents independently selected from halo, cyano, nitro, trifluoromethyl, trifluoromethoxy, azido, —$C(O)R^{11}$, —$C(O)OR^{11}$, —$OC(O)R^{11}$, —$NR^{11}C(O)R^{12}$, —$C(O)NR^{11}R^{12}$, —$NR^{11}R^{12}$, hydroxy, $C_1$–$C_6$ alkyl, and $C_1$–$C_6$ alkoxy;

each $R^{11}$ and $R^{12}$ is independently H or $C_1$–$C_6$ alkyl, and where $R^{11}$ and $R^{12}$ are as —$(CR^{11}R^{12})_q$ or —$(CR^{11}R^{12})_t$ each is independently defined for each iteration of q or t in excess 1;

$R^{13}$ is selected from the list of substituents provided in the definition of $R^{10}$ and —$SiR^{14}R^{15}R^{16}$; and, $R^{14}$, $R^{15}$ and $R^{16}$ are each independently selected from the substituents provided in the definition of $R^{10}$ except at least one of $R^{14}$, $R^{15}$ and $R^{16}$ is not H.

2. A compound according to claim 1 wherein said compound is a compound of formula 1; $R^1$ is H, $C_1$–$C_6$ alkyl, or cyclopropylmethyl; $R^2$ is H; and $R^6$ is —$NR^{10}R^{11}$, —$OR^{10}$, or a heterocyclic group selected from triazolyl, imidazolyl, pyrazolyl, and piperidinyl, wherein said heterocyclic group is optionally substituted by an $R^3$ group.

3. A compound according to claim 1 wherein said compound is a compound of formula 1, $R^7$ is imidazolyl optionally substituted by $C_1$–$C_6$ alkyl; $R^6$ is hydroxy, amino, or triazolyl; $R^8$ is phenyl substituted by 1 to 2 $R^3$ groups; and $R^4$, and $R^5$ are each independently selected from H and halo.

4. A compound according to claim 1 wherein said compound is a compound of formula 1, $R^1$ is —$(CR^{11}R^{12})_t$ ($C_3$–$C_{10}$ cycloalkyl) wherein t is an integer from 0 to 3; $R^2$ is H; and $R^6$ is —$NR^{10}R^{11}$, —$OR^{10}$, or a heterocyclic group selected from triazolyl, imidazolyl, pyrazolyl, and piperidinyl, wherein said heterocyclic group is optionally substituted by an $R^3$ group.

5. A compound according to claim 1 wherein $R^7$ is imidazolyl optionally substituted by $C_1$–$C_6$ alkyl; $R^6$ is hydroxy, amino, or triazolyl.

6. A compound according to claim 1 wherein said compound is a compound of formula 2; $R^2$ is H; $R^6$ is —$NR^{10}OR^{11}$, —$OR^{10}$ or triazolyl.

7. A compound according to claim 1 wherein said compound is a compound of formula 2, $R^7$ is imidazolyl optionally substituted by $C_1$–$C_6$ alkyl; $R^6$ is hydroxy or amino; $R^8$ is phenyl substituted by 1 to 2 $R^3$ groups; and $R^4$ and $R^5$ are each independently selected from H and halo.

8. A compound according to claim 1 wherein said compound is selected from the group consisting of:

(4-Chloro-phenyl)-[2-methoxy-4-(5-methyl-thiophen-2-yl)-quinolin-6-yl]-(3-methyl-3H-imidazol-4-yl)-methanol;

6-[(4-Chloro-phenyl)-hydroxy-(3-methyl-3H-imidazol-4-yl)-methyl]-1-methyl-4-(5-methyl-thiophen-2-yl)-1H-quinolin-2-one;

6-[Amino-(4-chloro-phenyl)-(3-methyl-3H-imidazol-4-yl)-methyl]-1-methyl-4-(5-methyl-thiophen-2-yl)-1H-quinolin-2-one;

6-[(4-Chloro-phenyl)-hydroxy-(3-methyl-3H-imidazol-4-yl)-methyl]-4-(5-chloro-thiophen-2-yl)-1-methyl-1H-quinolin-2-one;

and the pharmaceutically acceptable salts, solvates and prodrugs of the foregoing compounds.

9. A method of preparing a compound of formula 1 according to claim 1, wherein $R^1$ of formula 1 is H, which comprises hydrolysing a compound of formula 2'

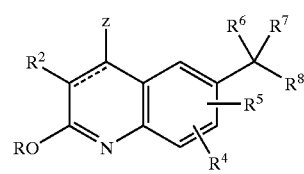

wherein R is $C_1$–$C_6$ alkyl and Z, $R^2$, $R^4$, $R^5$, $R^6$, $R^7$ and $R^8$ are as defined for formula 1 in claim 1.

10. A method of treating abnormal cell growth that responds to a ras farnesylation inhibitory, in a mammal in need of such treatment which comprises administering to said mammal a therapeutically effective amount of a compound according to claim 1.

11. A pharmaceutical composition which comprises a therapeutically effective amount of a compound according to claim 1 and a pharmaceutically acceptable carrier.

* * * * *